US009139743B2

United States Patent
Morimitsu et al.

(10) Patent No.: US 9,139,743 B2
(45) Date of Patent: *Sep. 22, 2015

(54) MALIC ACID DERIVATIVES AS AMORPHOUS MATERIALS FOR PHASE CHANGE INK

(71) Applicant: XEROX CORPORATION, Norwalk, CT (US)

(72) Inventors: Kentaro Morimitsu, Mississauga (CA); Adela Goredema, Oakville (CA); Naveen Chopra, Oakville (CA); Jennifer Belelie, Oakville (CA)

(73) Assignee: XEROX CORPORATION, Norwalk, CT (US)

( * ) Notice: Subject to any disclaimer, the term of this patent is extended or adjusted under 35 U.S.C. 154(b) by 122 days.

This patent is subject to a terminal disclaimer.

(21) Appl. No.: 13/756,334

(22) Filed: Jan. 31, 2013

(65) Prior Publication Data
US 2014/0208979 A1 Jul. 31, 2014

(51) Int. Cl.
C07C 69/34 (2006.01)
C07C 69/52 (2006.01)
C09D 7/12 (2006.01)
C09D 11/03 (2014.01)

(52) U.S. Cl.
CPC .............. C09D 7/1233 (2013.01); C09D 11/03 (2013.01)

(58) Field of Classification Search
CPC ................... C09D 7/2331; C09D 11/03
See application file for complete search history.

(56) References Cited

U.S. PATENT DOCUMENTS

| 2,121,617 | A | * | 6/1938 | Werntz ................... 558/32 |
| 4,490,731 | A | | 12/1984 | Vaught |
| 5,195,430 | A | | 3/1993 | Rise |
| 5,231,135 | A | | 7/1993 | Machell |
| 5,389,958 | A | | 2/1995 | Bui |
| 5,621,022 | A | | 4/1997 | Jaeger |
| 6,221,137 | B1 | | 4/2001 | King |

(Continued)

OTHER PUBLICATIONS

Stachurski, Z. Materials, 2011, 4, 1564-1598.*

(Continued)

Primary Examiner — Clinton Brooks
(74) Attorney, Agent, or Firm — Pillsbury Winthrop Shaw Pittman LLP

(57) ABSTRACT

Disclosed herein is a component that is substantially amorphous, the component comprising at least one non-ester material and at least one ester of malic acid having a formula of

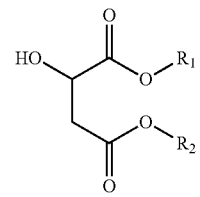

wherein $R_1$ and $R_2$ each, independently of the other, is an alkyl group, and further wherein the alkyl portion can be straight, branched or cyclic, saturated or unsaturated, substituted or unsubstituted, having from 1 to about 40 carbon atoms, an substituted or unsubstituted aromatic or heteroaromatic group, and mixtures thereof.

16 Claims, 3 Drawing Sheets

(56) References Cited

U.S. PATENT DOCUMENTS

| | | | |
|---|---|---|---|
| 6,472,523 | B1 | 10/2002 | Banning |
| 6,476,219 | B1 | 11/2002 | Duff |
| 6,576,747 | B1 | 6/2003 | Carlini |
| 6,576,748 | B1 | 6/2003 | Carlini |
| 6,590,082 | B1 | 7/2003 | Banning |
| 6,646,111 | B1 | 11/2003 | Carlini |
| 6,663,703 | B1 | 12/2003 | Wu |
| 6,673,139 | B1 | 1/2004 | Wu |
| 6,696,552 | B2 | 2/2004 | Mayo |
| 6,713,614 | B2 | 3/2004 | Carlini |
| 6,726,755 | B2 | 4/2004 | Titterington |
| 6,755,902 | B2 | 6/2004 | Banning |
| 6,821,327 | B2 | 11/2004 | Jaeger |
| 6,958,406 | B2 | 10/2005 | Banning |
| 7,053,227 | B2 | 5/2006 | Jaeger |
| 7,381,831 | B1 | 6/2008 | Banning |
| 7,427,323 | B1 | 9/2008 | Birau |
| 8,328,924 | B2 | 12/2012 | Morimitsu |
| 2012/0272862 | A1 | 11/2012 | Chopra |
| 2012/0272863 | A1 | 11/2012 | Morimitsu |
| 2012/0274698 | A1 | 11/2012 | Morimitsu |
| 2012/0309896 | A1 | 12/2012 | Carlini et al. |

OTHER PUBLICATIONS

U.S. Appl. No. 13/456,619, filed Apr. 26, 2012.
U.S. Appl. No. 13/456,916, filed Apr. 26, 2012.
U.S. Appl. No. 13/457,221, filed Apr. 26, 2012.
U.S. Appl. No. 13/457,323, filed Apr. 26, 2012.
U.S. Appl. No. 13/680,818, filed Nov. 19, 2012.
U.S. Appl. No. 13/681,106, filed Nov. 19, 2012.
Peredes et al., "Borederline Mechanisms Involving Ion-molecule Pairs for the Nucleophilic Substitution Reactions of Benzhydrol and Its Derivatives. Facile Formation and Cleavage of Diphenylmethyl Ethers for the Protection of Hydroxyl Groups." Tetrahedrom Letters 39 (1998) 2037-2038.
Pratt et al., "Reaction Rates by Distillation. I. The Etherification of Phenylcarbinols and the Transetherification of their Ethers" J. Am. Chem. Soc. 71, (1949) 2846-2849.

* cited by examiner

MALIC ACID DERIVATIVES AS AMORPHOUS MATERIALS FOR PHASE CHANGE INK

CROSS-REFERENCE TO RELATED APPLICATIONS

Reference is made to commonly owned and co-pending, U.S. patent application Ser. No. 13/756,308 entitled "Phase Change Ink Formulation Including Malic Acid Derivatives As Amorphous Materials" to Kentaro Morimitsu et al., electronically filed on the same day herewith, the entire disclosures of which are incorporated herein by reference in its entirety.

BACKGROUND

The present embodiments relate to malic acid derivatives as amorphous materials for phase change ink compositions (or solid inks) characterized by being solid at room temperature and molten at an elevated temperature at which the molten ink is applied to a substrate. These phase change ink compositions can be used for ink jet printing. The present embodiments are directed to an amorphous compound comprising an ester of malic acid, and methods of making the same.

Ink jet printing processes may employ inks that are solid at room temperature and liquid at elevated temperatures. Such inks may be referred to as solid inks, hot melt inks, phase change inks and the like. For example, U.S. Pat. No. 4,490,731, the disclosure of which is totally incorporated herein by reference, discloses an apparatus for dispensing phase change ink for printing on a recording medium such as paper. In piezo ink jet printing processes employing hot melt inks, the phase change ink is melted by the heater in the printing apparatus and utilized (jetted) as a liquid in a manner similar to that of conventional piezo ink jet printing. Upon contact with the printing recording medium, the molten ink solidifies rapidly, enabling the colorant to substantially remain on the surface of the recording medium instead of being carried into the recording medium (for example, paper) by capillary action, thereby enabling higher print density than is generally obtained with liquid inks. Advantages of a phase change ink in ink jet printing are thus elimination of potential spillage of the ink during handling, a wide range of print density and quality, minimal paper cockle or distortion, and enablement of indefinite periods of nonprinting without the danger of nozzle clogging, even without capping the nozzles.

In general, phase change inks (sometimes referred to as "hot melt inks") are in the solid phase at ambient temperature, but exist in the liquid phase at the elevated operating temperature of an ink jet printing device. At the jetting temperature, droplets of liquid ink are ejected from the printing device and, when the ink droplets contact the surface of the recording medium, either directly or via an intermediate heated transfer belt or drum, they quickly solidify to form a predetermined pattern of solidified ink drops.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes or pigments, namely, cyan, magenta, yellow and black, although the inks are not limited to these four colors. These subtractive primary colored inks can be formed by using a single dye or pigment or a mixture of dyes or pigments.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording medium (for example, paper, transparency material, and the like), the droplets solidify immediately upon contact with the recording medium, so that migration of ink along the printing medium is prevented and dot quality is improved.

While the above conventional phase change ink technology is generally successful in producing vivid images and providing economy of jet use and substrate latitude on porous papers, such technology has not been satisfactory for coated substrates. Thus, while known compositions and processes are suitable for their intended purposes, a need remains for additional means for forming images or printing on coated paper substrates. As such, there is a need to find alternative compositions for phase change ink compositions, specifically those derived from biorenewable source, and future printing technologies to provide customers with excellent image quality on all substrates. There is further a need to provide such phase change ink compositions which are suitable for fast printing environments like production printing.

Each of the foregoing U.S. patents and patent publications are incorporated by reference herein. Further, the appropriate components and process aspects of the each of the foregoing U.S. patents and patent publications may be selected for the present disclosure in embodiments thereof.

SUMMARY

The present disclosure relates to novel amorphous components and related phase change ink compositions. The phase change ink compositions may include the amorphous and possible crystalline components and may be ink-jet printed on coated or un-coated substrates.

According to embodiments illustrated herein, there is provided an amorphous component that may be synthesized from malic acid.

In particular, the present embodiments provide a component that is substantially amorphous, the component comprising at least one non-ester material and at least one ester of malic acid having a formula of

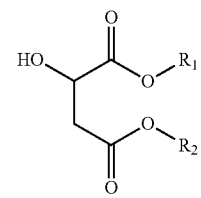

wherein $R_1$ and $R_2$ each, independently of the other, is an alkyl group, and further wherein the alkyl portion can be straight, branched or cyclic, saturated or unsaturated, substituted or unsubstituted, having from 1 to about 40 carbon atoms, an substituted or unsubstituted aromatic or heteroaromatic group, and mixtures thereof.

In other embodiments, there is provided a method of forming a component, the method comprising: selecting at least one alcohol; reacting the at least one alcohol with a malic acid; and controlling one or more reaction conditions to form the component that is substantially amorphous, wherein the component comprises at least one non-ester material and at least one ester of malic acid having a formula of

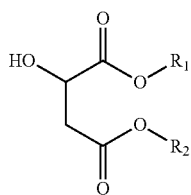

wherein $R_1$ and $R_2$ each, independently of the other, is an alkyl group, and further wherein the alkyl portion can be straight, branched or cyclic, saturated or unsaturated, substituted or unsubstituted, having from 1 to about 40 carbon atoms, an substituted or unsubstituted aromatic or heteroaromatic group, and mixtures thereof.

BRIEF DESCRIPTION OF THE DRAWINGS

For a better understanding of the present embodiments, reference may be had to the accompanying figures.

DETAILED DESCRIPTION

Figure 1:
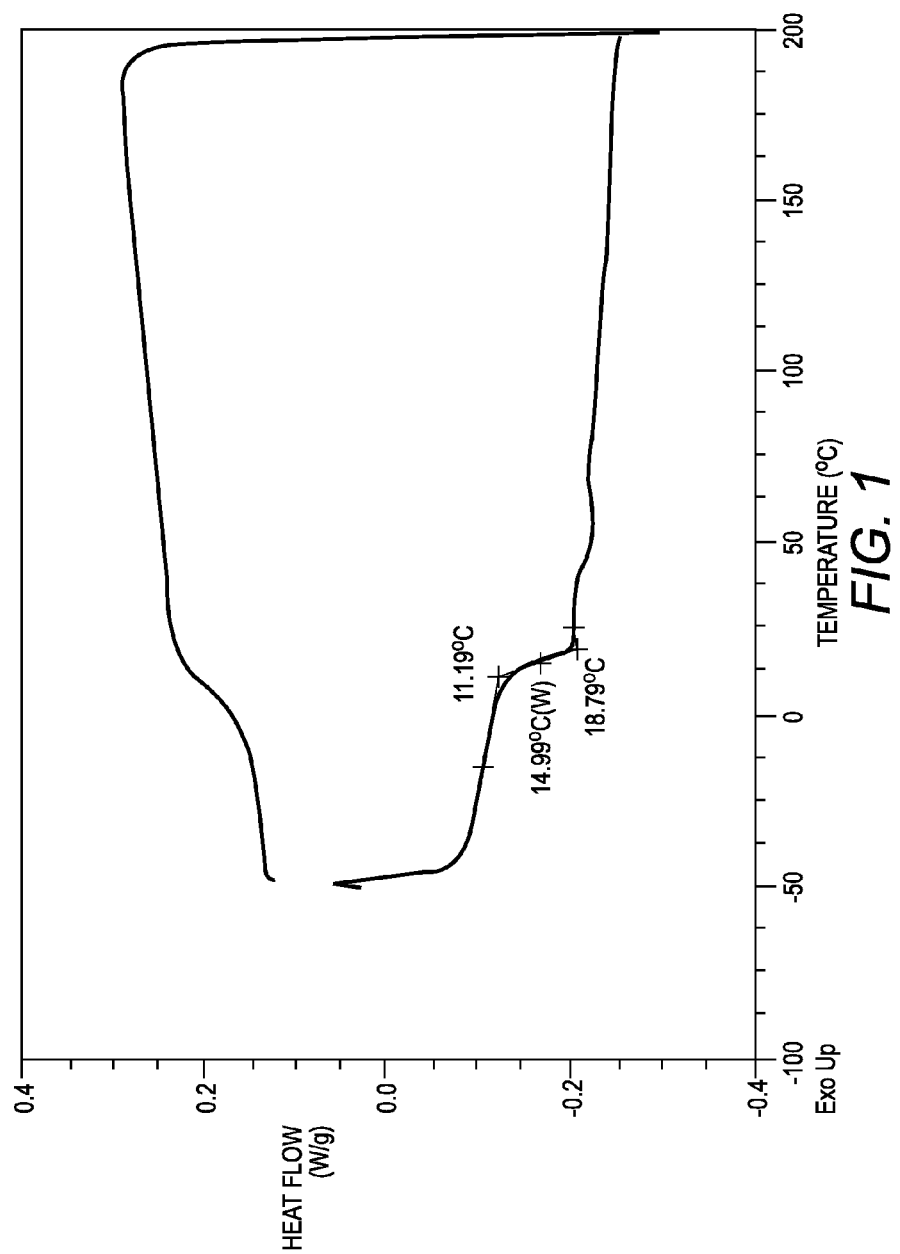
FIG. 1 is differential scanning calorimetry (DSC) data of an exemplary amorphous component upon heating and cooling.

In the following description, it is understood that other embodiments may be utilized and structural and operational changes may be made without departure from the scope of the present embodiments disclosed herein.

The present embodiments provide an amorphous component and/or the related phase change ink composition, e.g., for ink jet printing, which includes an amorphous component comprising at least one non-ester material and at least one ester of malic acid having a formula of

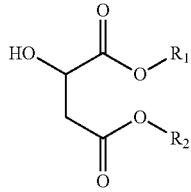

wherein $R_1$ and $R_2$ each, independently of the other, is an alkyl group, and further wherein the alkyl portion can be straight, branched or cyclic, saturated or unsaturated, substituted or unsubstituted, having from 1 to about 40 carbon atoms, or from 1 to 20 carbon atoms, or from 1 to 15 carbon atoms, an substituted or unsubstituted aryl or heteroaryl group, and mixtures thereof.

The substituents on the substituted alkyl, aryl, heteroaryl groups can be (but are not limited to) alkyl groups, alkoxy groups, phenyl groups, phenyloxy groups, hydroxy groups, halogen atoms, amine groups, pyridine groups, pyridinium groups, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, sulfone groups, acyl groups, acid anhydride groups, azo groups, azide groups, cyanato groups, isocyanato groups, thiocyanato groups, isothiocyanato groups, and mixtures thereof. The substituents on the substituted alkyl, aryl, heteroaryl groups may be further substituted as defined herein.

The term "alkyl," as used herein, alone or in combination, refers to a straight-chain alkyl radical, branched-chain alkyl radical, or cyclic alkyl radical containing from 1 to and 40, from 1 to 20, and or from 1 to 15 carbon atoms. The cyclic alkyl radical include fused cyclic alkyl radical. Examples of alkyl radicals include, but not limited to, methyl, ethyl, n-propyl, isopropyl, n-butyl, isobutyl, sec-butyl, tert-butyl, pentyl, iso-amyl, hexyl, octyl, noyl and the like. Examples of cyclic alkyl radicals include, but not limited to, $C_{3-8}$ cycloalky (e.g., cyclohexyl or cyclopenyl). Alkyl groups may be optionally substituted as defined herein.

The term "aryl," as used herein, alone or in combination, refers to a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "heteroaryl." as used herein, alone or in combination, refers to "aryl" which has one or more heteroatoms in the ring or ring system. The term "heteroaryl" embraces aromatic radicals such as pyridinyl, furyl, thienyl, oxazolyl, thiazolyl, imidazolyl, indolyl, quinolinyl, benzofuranyl, benzothienyl, benzooxazolyl, benzothiazolyl, and benzoimidazolyl.

In some embodiments, the amorphous component may be combinations of various compounds. For example, the amorphous component may include at least one ester of malic acid derivative having the structure of formula (I) and/or one or more non-ester derivatives. Such amorphous component, in some embodiments, may be obtained from reactions of malic acid and alcohols. The reaction scheme below illustrates a method of the preparation of the malic acid derivatives:

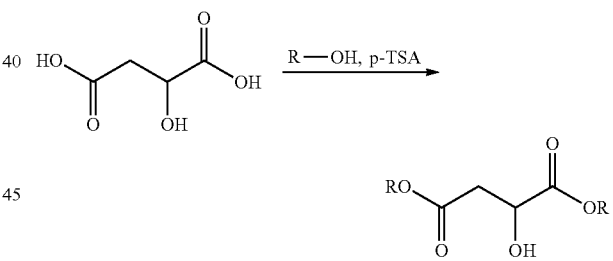

wherein each R is independently an alkyl group, and further wherein the alkyl portion can be straight, branched or cyclic, saturated or unsaturated, substituted or unsubstituted, having from 1 to about 40 carbon atoms, an substituted or unsubstituted aromatic or heteroaromatic group, and mixtures thereof. The amorphous component of malic acid can be achieved by reacting about 1 equivalent mole of malic acid with from about 1 to about 5 equivalent mole of alcohol. In certain embodiments, about 1 equivalent mole of alcohol may be used in the reaction. In certain embodiments, about 2 equivalent moles of alcohol may be used in the reaction. In certain embodiments, about 3 equivalent moles of alcohol may be used in the reaction.

The malic acid(s) may include, for example, a DL-malic acid, D-malic acid, L-malic acid, other stereoisomers of malic acid, and/or mixtures thereof.

Alcohols suitable for use in the present disclosure include those that can react with malic acid and form amorphous material that is non-crystalline. Non-limiting examples of alcohols may include:

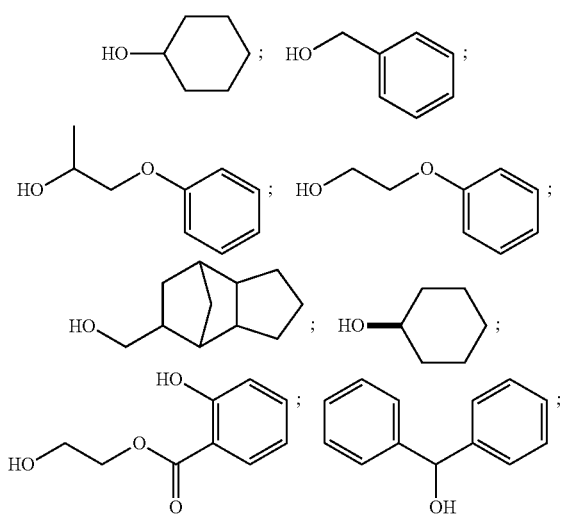

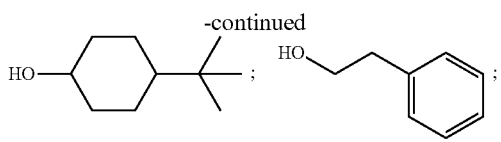

and mixtures thereof. In certain embodiments, the amorphous component includes malic acid derivatives prepared from an alcohol including benzhydrol.

In certain embodiments, the at least one non-ester material and the at least one ester of malic acid may be reaction products from the malic acid and one or more alcohols.

In certain embodiments, DL-malic acid may react with benzhydrol to generate products that include one or more ester of malic acid derivatives and one or more non-ester of malic acid derivatives, for example, as depicted in Scheme 1. The reaction products and their ratios may be determined by controlling reaction conditions, such as ratio of alcohols to acid, acidic conditions, reaction temperatures, solvent, etc. In one embodiment, the reaction solvent may be xylene (bp=about 140° C.), and the reaction temperature may be at least about 60° C.

Scheme 1

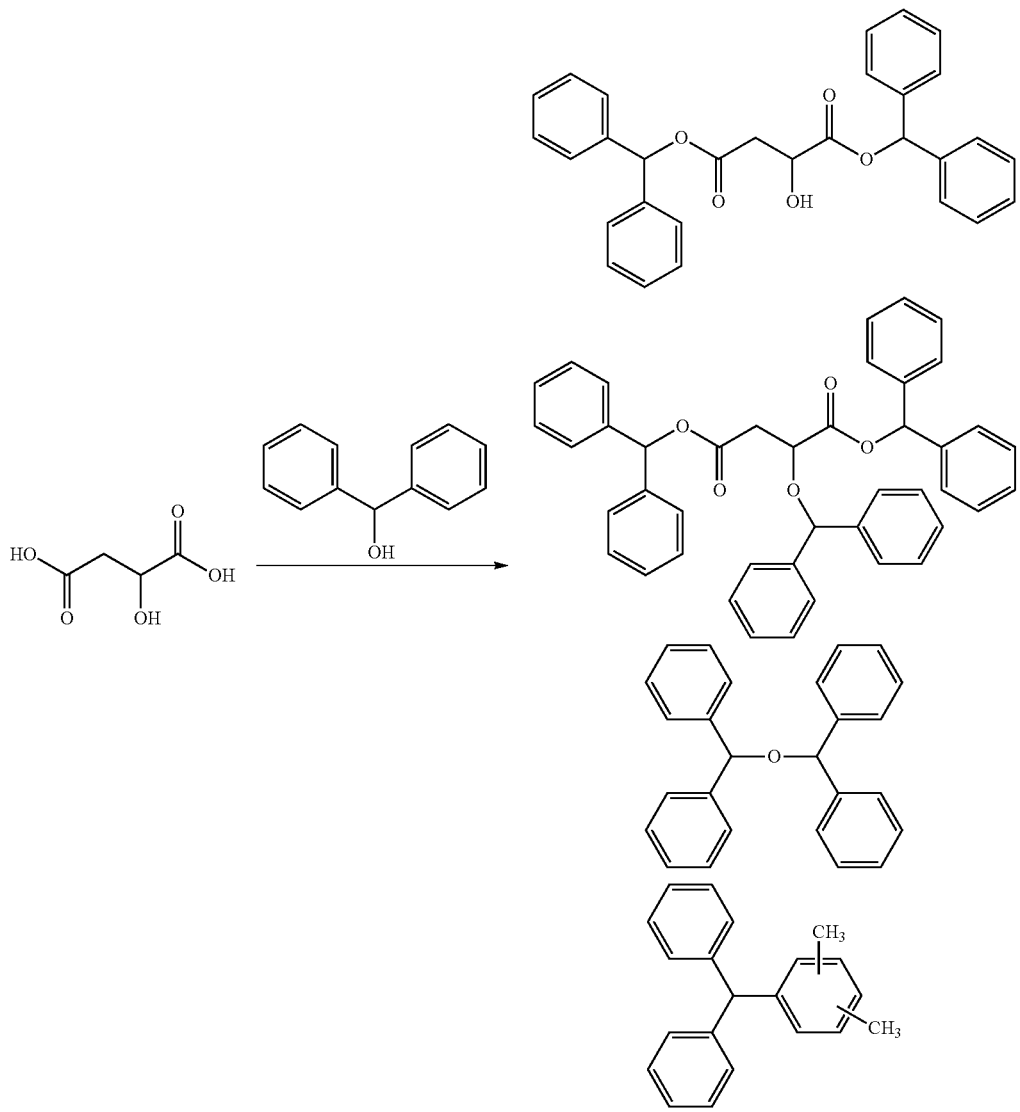

In a specific embodiment shown in Scheme 1, the reaction can be performed under acidic condition, where benzhydrol forms stable carbocation which reacts with alcohol and aromatic solvent (such as xylenes) to form dibenzhydryl ethers and substituted triarylmethane. See, *Tetrahedron Lett.*, 39, 2037-2038 (1998); and *J. Am. Chem. Soc.*, 71, 2846-2849 (1949). The amorphous component in the ink formulation may comprise more than one compound, for example, including side products from a reaction. As long as the properties of the materials (e.g., mixture of reaction products) are appropriate, such materials may be considered as the amorphous component in the ink formulation.

Generally, differential scanning calorimetry (DSC) data may be used to determine if a material is in an amorphous state. For example, FIG. 1 depicts a DSC result for an example shown in Scheme 1, where the material shows glass transition peak without showing crystallization peak, indicating an amorphous state. In addition, rheological curves may be used to determine viscosity of the amorphous component.

The amorphous materials show no crystallization, have relatively low viscosity ($<10^2$ cps, or from about 1 cps to about 100 cps, or from about 5 cps to about 95 cps) at high temperatures (e.g., jetting range from about 100° C. to about 140° C.), but very high viscosity ($>10^5$ cps, or from about $10^5$ cps to about $10^{10}$ cps) at room temperature. The characteristics of these amorphous materials are beneficial in the preparation of phase change inks of the present embodiments, because the low viscosity at about 140° C. of the above components provide wide formulation latitude, and the high viscosity at room temperature imparts robustness.

In certain embodiments, the phase change ink composition includes a crystalline material which is suitable for ink jet phase change ink. Various crystalline components can be mixed with the amorphous component to form phase change ink formations. The crystalline components may include, for example, ester (see U.S. Patent Application Publication Nos. US20120272862, US20120272863, US20120274698, and U.S. patent application Ser. Nos. 13/681,106, and 13/680,818), amide (see U.S. patent application Ser. Nos. 13/457,221 and U.S. Pat. No. 8,328,924), urethane (see U.S. patent application Ser. No. 13/456,619), aromatic ethers (see U.S. patent application Ser. No. 13/456,916), and sulfones (see U.S. patent application Ser. No. 13/457,323), the disclosures of which are totally incorporate herein by reference.

In certain embodiments, the crystalline component may be a diurethane having a general formula:

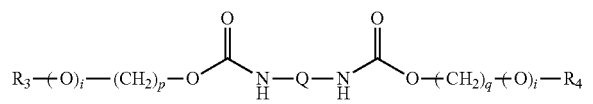

wherein Q is alkanediyl; each $R_3$ and $R_4$ is independently phenyl or cyclohexyl optionally substituted with one or more alkyl; i is 0 or 1; j is 0 or 1; p is 1 to 4; q is 1 to 4. In certain of such embodiments, each $R_3$ and $R_4$ is independently phenyl or cyclohexyl optionally substituted with one or more methyl or ethyl. In certain of such embodiments, $R_3$ and $R_4$ is phenyl. In certain embodiments, Q is —(CH$_2$)$_n$— and n is 4 to 8. In certain of such embodiments, n is 6, as depicted in U.S. patent application Ser. No. 13/456,619, which is hereby incorporated by reference in its entirety.

In certain embodiments, the crystalline component may be an ester of an aliphatic linear diacid having the following structure:

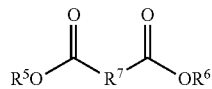

wherein $R^7$ may be substituted or unsubstituted alkyl chain and is selected from the group consisting of —(CH$_2$)$_1$— to —(CH$_2$)$_{12}$—, and wherein $R^5$ and $R^6$, each, independently of the other or meaning that they can be the same or different, is selected from the group consisting of an alkyl group, wherein the alkyl portion can be straight, branched or cyclic, saturated or unsaturated, substituted or unsubstituted, having from about 1 to about 40 carbon atoms, or an substituted or unsubstituted aromatic or heteroaromatic group, and mixtures thereof, as depicted in U.S. Patent Application Publication No. US20120272862, which is hereby incorporated by reference in its entirety.

In certain embodiments, the crystalline component may be an esters of tartaric acid having the formula:

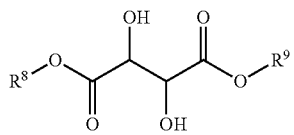

wherein $R^8$ and $R^9$ each, independently of the other or meaning that they can be the same or different, is selected from the group consisting of alkyl group, wherein the alkyl portion can be straight, branched or cyclic, saturated or unsaturated, substituted or unsubstituted, having from about 1 to about 40 carbon atoms, or an substituted or unsubstituted aromatic or heteroaromatic group, and mixtures thereof. The tartaric acid backbone is selected from L-(+)-tartaric acid, D-(−)-tartaric acid, DL-tartaric acid, or mesotartaric acid, and mixtures thereof, as depicted in U.S. Patent Application Publication No. US20120272863, which is hereby incorporated by reference in its entirety.

In certain embodiments, the crystalline component may be an amide having the following structure:

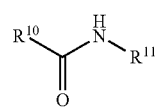

wherein $R^{10}$ and $R^{11}$ each, independently of the other or meaning that they can be the same or different, is selected from the group consisting of alkyl group, wherein the alkyl portion can be straight, branched or cyclic, saturated or unsaturated, substituted or unsubstituted, having from about 1 to about 40 carbon atoms, or an substituted or unsubstituted aromatic or heteroaromatic group, and mixtures thereof, as depicted in U.S. Pat. No. 8,328,924, which is hereby incorporated by reference in its entirety.

Resulting inks incorporating an amorphous component of the present embodiments demonstrate excellent robustness on uncoated and coated substrates. The resulting ink compositions also show good rheological profiles and improved performance in inks. Image samples created by the phase change ink composition on coated paper by K-proof demonstrated remarkable robustness. Furthermore, the amorphous component of the present embodiments has additional advantages of being obtained from a potential bio-derived ("green") source.

A K-printing proofer is a common test fixture in a print shop. In this case, the K-printing proofer has been modified to heat the printing plate to melt the phase change ink. The K-printing proofer used has three rectangular gravure patterns each approximately 9.4×4.7 cm. The cell density of the first rectangle is nominally 100%, the second 80%, and the third 60%. In practice this K-printing proof plate results in films (or pixels) of about 5 microns in thickness (or height). Test ink is spread over the heated gravure plate and a test print is made by passing a wiping blade across the plate surface immediately followed by a rubber roll upon which a test paper has been secured. As the paper roll passes ink is transferred from the gravure cells to the paper.

The ink composition, in specific embodiments, further comprises a colorant, which may be a pigment or dye, present in the ink composition in an amount of from about 0.1 percent to about 50 percent by weight, or from about 0.2 percent to about 20 percent by weight of the total weight of the ink composition.

The amorphous component is present in an amount of from about 5 percent to about 40 percent by weight, or from about 5 percent to about 35 percent by weight of the total weight of the ink composition. The crystalline component may be present in an amount of from about 60 percent to about 95 percent by weight, or from about 65 percent to about 95 percent by weight of the total weight of the ink composition.

In embodiments, the resulting phase change ink has a viscosity of from about 1 to about 22 cps, from about 4 to about 15 cps, or from about 6 to about 12 cps, at a jetting temperature. The jetting temperature is typically comprised in a range from about 100° C. to about 140° C. In embodiments, the phase change ink has a viscosity of at least about $10^6$ cps at room temperature The phase change ink (or solid ink) of the present embodiments may further include conventional additives to take advantage of the known functionality associated with such conventional additives. Such additives may include, for example, at least one antioxidant, defoamer, slip and leveling agents, clarifier, viscosity modifier, adhesive, plasticizer and the like.

The phase change ink may optionally contain antioxidants to protect the images from oxidation and also may protect the ink components from oxidation while existing as a heated melt in the ink reservoir. Examples of suitable antioxidants include N,N'-hexamethylene bis(3,5-di-tert-butyl-4-hydroxy hydrocinnamamide) (IRGANOX 1098, available from BASF); 2,2-bis(4-(2-(3,5-di-tert-butyl-4-hydroxyhydrocinnamoyloxy)) ethoxyphenyl)propane (TOPANOL-205, available from Vertellus); tris(4-tert-butyl-3-hydroxy-2,6-dimethyl benzyl)isocyanurate (Aldrich), 2,2'-ethylidene bis(4,6-di-tert-butylphenyl)fluoro phosphonite (ETHANOX-398, available from Albermarle Corporation); tetrakis(2,4-di-tert-butylphenyl)-4,4'-biphenyl diphosphonite (Aldrich); pentaerythritol tetrastearate (TCI America); tributylammonium hypophosphite (Aldrich); 2,6-di-tert-butyl-4-methoxyphenol (Aldrich); 2,4-di-tert-butyl-6-(4-methoxybenzyl)phenol (Aldrich); 4-bromo-2,6-dimethylphenol (Aldrich); 4-bromo-3,5-didimethylphenol (Aldrich); 4-bromo-2-nitrophenol (Aldrich); 4-(diethyl aminomethyl)-2,5-dimethylphenol (Aldrich); 3-dimethylaminophenol (Aldrich); 2-amino-4-tert-amylphenol (Aldrich); 2,6-bis(hydroxymethyl)-p-cresol (Aldrich), 2,2'-methylenediphenol (Aldrich); 5-(diethylamino)-2-nitrosophenol (Aldrich); 2,6-dichloro-4-fluorophenol (Aldrich); 2,6-dibromo fluoro phenol (Aldrich), α-trifluoro-o-cresol (Aldrich); 2-bromo-4-fluorophenol (Aldrich); 4-fluorophenol (Aldrich); 4-chlorophenyl-2-chloro-1,1,2-tri-fluoroethyl sulfone (Aldrich); 3,4-difluoro phenylacetic acid (Adrich); 3-fluorophenylacetic acid (Aldrich); 3,5-difluoro phenylacetic acid (Aldrich); 2-fluorophenylacetic acid (Aldrich); 2,5-bis(trifluoromethyl)benzoic acid (Aldrich); ethyl-2-(4-(4-(trifluoromethyl)phenoxy)phenoxy)propionate (Aldrich); tetrakis(2,4-di-tert-butyl phenyl)-4,4'-biphenyl diphosphonite (Aldrich); 4-tert-amyl phenol (Aldrich), 3-(2H-benzotriazol-2-yl)-4-hydroxy phenethylalcohol (Aldrich); NAUGARD 76, NAUGARD 445, NAUGARD 512, AND NAUGARD 524 (manufactured by Chemtura Corporation), and the like, as well as mixtures thereof. The antioxidant, when present, may be present in the ink in any desired or effective amount, such as from about 0.25 percent to about 10 percent by weight of the ink or from about 1 percent to about 5 percent by weight of the ink.

In embodiments, the phase change ink compositions described herein also include a colorant. The ink of the present embodiments can thus be one with or without colorants. Any desired or effective colorant can be employed in the phase change ink compositions, including dyes, pigments, mixtures thereof, and the like, provided that the colorant can be dissolved or dispersed in the ink carrier. Any dye or pigment may be chosen, provided that it is capable of being dispersed or dissolved in the ink carrier and is compatible with the other ink components. The phase change carrier compositions can be used in combination with conventional phase change ink colorant materials, such as Color Index (C.I.) Solvent Dyes, Disperse Dyes, modified Acid and Direct Dyes, Basic Dyes, Sulphur Dyes, Vat Dyes, and the like. Examples of suitable dyes include Neozapon Red 492 (BASF); Orasol Red G (Pylam Products); Direct Brilliant Pink B (Oriental Giant Dyes); Direct Red 3BL (Classic Dyestuffs); Supranol Brilliant Red 3BW (Bayer AG); Lemon Yellow 6G (United Chemie); Light Fast Yellow 3G (Shaanxi); Aizen Spilon Yellow C-GNH (Hodogaya Chemical); Bemachrome Yellow GD Sub (Classic Dyestuffs); Cartasol Brilliant Yellow 4GF (Clariant); Cibanone Yellow 2G (Classic Dyestuffs); Orasol Black RLI (BASF); Orasol Black CN (Pylam Products); Savinyl Black RLSN (Clariant); Pyrazol Black BG (Clariant); Morfast Black 101 (Rohm & Haas); Diaazol Black RN (ICI); Thermoplast Blue 670 (BASF); Orasol Blue GN (Pylam Products); Savinyl Blue GLS (Clariant); Luxol Fast Blue MBSN (Pylam Products); Sevron Blue 5GMF (Classic Dyestuffs); Basacid Blue 750 (BASF); Keyplast Blue (Keystone Aniline Corporation); Neozapon Black X51 (BASF); Classic Solvent Black 7 (Classic Dyestuffs); Sudan Blue 670 (C.I. 61554) (BASF); Sudan Yellow 146 (C.I. 12700) (BASF); Sudan Red 462 (C.I. 26050) (BASF); C.I. Disperse Yellow 238; Neptune Red Base NB543 (BASF, C.I. Solvent Red 49); Neopen Blue FF-4012 (BASF); Fatsol Black BR(C.I. Solvent Black 35) (Chemische Fabriek Triade BV); Morton Morplas Magenta 36 (C.I. Solvent Red 172); metal phthalocyanine colorants such as those disclosed in U.S. Pat. No. 6,221,137, the disclosure of which is totally incorporated herein by reference, and the like. Polymeric dyes can also be used, such as those disclosed in, for example, U.S. Pat. No. 5,621,022 and U.S. Pat. No. 5,231,135, the disclosures of each of which are herein entirely incorporated herein by reference, and commercially available from, for example, Milliken & Company as Milliken Ink Yellow 869, Milliken Ink Blue 92, Milliken Ink Red 357, Milliken Ink Yellow 1800, Milliken Ink Black 8915-67, uncut Reactint Orange X-38, uncut Reactint Blue X-17, Solvent Yellow 162, Acid Red 52, Solvent Blue 44, and uncut Reactint Violet X-80.

Pigments are also suitable colorants for the phase change inks. Examples of suitable pigments include PALIOGEN Violet 5100 (BASF); PALIOGEN Violet 5890 (BASF); HELIOGEN Green L8730 (BASF); LITHOL Scarlet D3700 (BASF); SUNFAST Blue 15:4 (Sun Chemical); Hostaperm Blue B2G-D (Clariant); Hostaperm Blue B4G (Clariant); Permanent Red P-F7RK; Hostaperm Violet BL (Clariant); LITHOL Scarlet 4440 (BASF); Bon Red C (Dominion Color Company); ORACET Pink RF (BASF); PALIOGEN Red 3871 K (BASF); SUNFAST Blue 15:3 (Sun Chemical); PALIOGEN Red 3340 (BASF); SUNFAST Carbazole Violet 23 (Sun Chemical); LITHOL Fast Scarlet L4300 (BASF); SUNBRITE Yellow 17 (Sun Chemical); HELIOGEN Blue L6900, L7020 (BASF); SUNBRITE Yellow 74 (Sun Chemical); SPECTRA PAC C Orange 16 (Sun Chemical); HELIOGEN Blue K6902, K6910 (BASF); SUNFAST Magenta 122 (Sun Chemical); HELIOGEN Blue D6840, D7080 (BASF); Sudan Blue OS (BASF); NEOPEN Blue FF4012 (BASF); PV Fast Blue B2GO1 (Clariant); IRGALITE Blue GLO (BASF); PALIOGEN Blue 6470 (BASF); Sudan Orange G (Aldrich), Sudan Orange 220 (BASF); PALIOGEN Orange 3040 (BASF); PALIOGEN Yellow 152, 1560 (BASF); LITHOL Fast Yellow 0991 K (BASF); PALIOTOL Yellow 1840 (BASF); NOVOPERM Yellow FGL (Clariant); Ink Jet Yellow 4G VP2532 (Clariant); Toner Yellow HG (Clariant); Lumogen Yellow D0790 (BASF); Suco-Yellow L1250 (BASF); Suco-Yellow D1355 (BASF); Suco Fast Yellow D1355, D1351 (BASF); HOSTAPERM Pink E 02 (Clariant); Hansa Brilliant Yellow 5GX03 (Clariant); Permanent Yellow GRL 02 (Clariant); Permanent Rubine L6B 05 (Clariant); FANAL Pink D4830 (BASF); CINQUASIA Magenta (DU PONT); PALIOGEN Black L0084 (BASF); Pigment Black K801 (BASF); and carbon blacks such as REGAL 33Q™ (Cabot), Nipex 150 (Evonik) Carbon Black 5250 and Carbon Black 5750 (Columbia Chemical), and the like, as well as mixtures thereof.

Pigment dispersions in the ink base may be stabilized by synergists and dispersants. Generally, suitable pigments may be organic materials or inorganic. Magnetic material-based pigments are also suitable, for example, for the fabrication of robust Magnetic Ink Character Recognition (MICR) inks. Magnetic pigments include magnetic nanoparticles, such as for example, ferromagnetic nanoparticles.

Also suitable are the colorants disclosed in U.S. Pat. No. 6,472,523, U.S. Pat. No. 6,726,755, U.S. Pat. No. 6,476,219, U.S. Pat. No. 6,576,747, U.S. Pat. No. 6,713,614, U.S. Pat. No. 6,663,703, U.S. Pat. No. 6,755,902, U.S. Pat. No. 6,590,082, U.S. Pat. No. 6,696,552, U.S. Pat. No. 6,576,748, U.S. Pat. No. 6,646,111, U.S. Pat. No. 6,673,139, U.S. Pat. No. 6,958,406, U.S. Pat. No. 6,821,327, U.S. Pat. No. 7,053,227, U.S. Pat. No. 7,381,831 and U.S. Pat. No. 7,427,323, the disclosures of each of which are incorporated herein by reference in their entirety.

In embodiments, solvent dyes are employed. An example of a solvent dye suitable for use herein may include spirit soluble dyes because of their compatibility with the ink carriers disclosed herein. Examples of suitable spirit solvent dyes include Neozapon Red 492 (BASF); Orasol Red G (Pylam Products); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow 5RA EX (Classic Dyestuffs); Orasol Black RLI (BASF); Orasol Blue GN (Pylam Products); Savinyl Black RLS (Clariant); Morfast Black 101 (Rohm and Haas); Thermoplast Blue 670 (BASF); Savinyl Blue GLS (Sandoz); Luxol Fast Blue MBSN (Pylam); Sevron Blue 5GMF (Classic Dyestuffs); Basacid Blue 750 (BASF); Keyplast Blue (Keystone Aniline Corporation); Neozapon Black X51 (C.I. Solvent Black, C.I. 12195) (BASF); Sudan Blue 670 (C.I. 61554) (BASF); Sudan Yellow 146 (C.I. 12700) (BASF); Sudan Red 462 (C.I. 260501) (BASF), mixtures thereof and the like. The colorant may be present in the phase change ink in any desired or effective amount to obtain the desired color or hue such as, for example, at least from about 0.1 percent by weight of the ink to about 50 percent by weight of the ink, at least from about 0.2 percent by weight of the ink to about 20 percent by weight of the ink, and at least from about 0.5 percent by weight of the ink to about 10 percent by weight of the ink.

In embodiments, the ink carriers for the phase change inks may have a viscosity of from about 1 to about 22 cps, or from about 4 to about 15 cps, or from about 6 to about 12 cps, at a the jetting temperature. The jetting temperature is typically comprised in a range from about 100° C. to about 140° C. In embodiments, the solid ink has a viscosity of about >$10^6$ cps, at room temperature. In embodiments, the solid ink has a melting temperature ($T_{melt}$) of from about 65 to about 150° C., or from about 70 to about 140° C., from about 80 to about 135° C. and a crystallizing temperature ($T_{crys}$) of from about 40 to about 140° C., or from about 45 to about 130° C., from about 50 to about 120° C., as determined by DSC at a rate of 10° C./min.

The ink compositions can be prepared by any desired or suitable method. For example, each of the components of the ink carrier can be mixed together, followed by heating, the mixture to at least its melting point, for example from about 60° C. to about 150° C., 80° C. to about 145° C. and 85° C. to about 140° C. The colorant may be added before the ink ingredients have been heated or after the ink ingredients have been heated. When pigments are the selected colorants, the molten mixture may be subjected to grinding in an attritor or media mill apparatus or other high energy mixing equipment to affect dispersion of the pigment in the ink carrier. The heated mixture is then stirred for about 5 seconds to about 30 minutes or more, to obtain a substantially homogeneous, uniform melt, followed by cooling the ink to ambient temperature (typically from about 20° C. to about 25° C.). The inks are solid at ambient temperature. The inks can be employed in apparatus for direct printing ink jet processes and in indirect (offset) printing ink jet applications. Another embodiment disclosed herein is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195,430, the disclosure of which is totally incorporated herein by reference. Yet another embodiment disclosed herein is directed to a process which comprises incorporating an ink as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. In another specific embodiment, both the intermediate transfer member and the final recording sheet are heated; in this embodiment, both the intermediate transfer member and the final recording sheet are heated to a temperature below that of the melted ink in the printing apparatus; in this embodiment, the relative temperatures of the intermediate transfer member and the final recording sheet can be (1) the intermediate transfer member is heated to a temperature above that of the final recording substrate and below that of the melted ink in the printing apparatus; (2) the final recording substrate is heated to a temperature above that of the intermediate transfer member and below that of the melted ink in the printing apparatus; or (3) the intermediate transfer member and the final recording sheet are heated to approximately the same temperature. An offset or indirect printing process is also disclosed in, for example, U.S. Pat. No. 5,389,958, the disclosure of which is totally incorporated herein by reference. In one specific embodiment, the printing apparatus employs a piezoelectric printing process wherein droplets of the ink are caused to be ejected in imagewise pattern by oscillations of piezoelectric vibrating elements. Inks as disclosed herein can also be employed in other hot melt printing processes, such as hot melt acoustic ink jet printing, hot melt thermal ink jet printing, hot melt continuous stream or deflection ink jet printing, and the like. Phase change inks as disclosed herein can also be used in printing processes other than hot melt ink jet printing processes.

Any suitable substrate or recording sheet can be employed, including plain papers such as XEROX 4200 papers, XEROX Image Series papers, Courtland 4024 DP paper, ruled notebook paper, bond paper, silica coated papers such as Sharp Company silica coated paper, JuJo paper, HAMMERMILL LASERPRINT paper, and the like, glossy coated papers such as XEROX Digital Color Elite Gloss, Sappi Warren Papers LUSTROGLOSS, specialty papers such as Xerox DURAPAPER, and the like, transparency materials, fabrics, textile products, plastics, polymeric films, inorganic recording mediums such as metals and wood, and the like, transparency materials, fabrics, textile products, plastics, polymeric films, inorganic substrates such as metals and wood, and the like.

The inks described herein are further illustrated in the following examples. All parts and percentages are by weight unless otherwise indicated.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

EXAMPLES

The examples set forth herein below and are illustrative of different compositions and conditions that can be used in practicing the present embodiments. All proportions are by weight unless otherwise indicated. It will be apparent, however, that the present embodiments can be practiced with many types of compositions and can have many different uses in accordance with the disclosure above and as pointed out hereinafter.

Example 1

Screening and Synthesis of Materials

DL-malic acid was selected as a backbone material. An esterification was conducted by a simple one-step reaction. Varieties of alcohols were reacted with DL-malic acid to form the corresponding diesters.

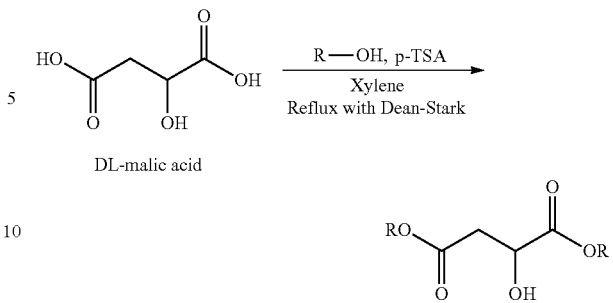

DL-malic acid

The following alcohols have been employed in the synthesis according to the reaction scheme shown above:

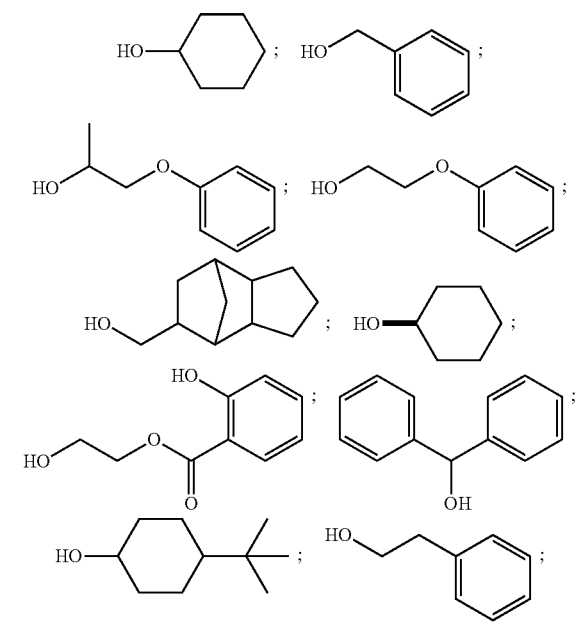

and mixtures thereof.

Synthetic Procedure of Amorphous Components from DL-Malic Acid and Benzhydrol (Amorphous A):

In a 500 mL flask, equipped with a Dean-Stark trap, DL-malic acid (15.0 g, 112 mmol), benzhydrol (41.2 g, 224 mmol), and xylene (150 ml) were added to give a suspension. p-Toluenesulfonic acid monohydrate (0.43 g, 2.2 mmol) was added and the mixture was refluxed for 2 hours with azeotropic removal of water. The reaction mixture was cooled down to room temperature and washed with $NaHCO_3$ aq. (1×) and brine (1×), then dried over $MgSO_4$. After filtration and removal of the solvent, the residue was dried under vacuum with stirring at 100° C. to obtain 44.0 g of amorphous solid. The sample was characterized by $^1$H NMR and acid number analysis (4.9 mgKOH/g).

$^1$H NMR analysis of Amorphous A revealed that four major products (see Scheme 1 as disclosed herein). When 3 eq. of benzhydrol was reacted with DL-malic acid, a reaction product, Amorphous B, was also amorphous and $^1$H NMR showed higher dibenzhydryl ether content in the mixture.

Material Properties

Differential scanning calorimetry (DSC) data of Amorphous A showed glass transition and no crystallization peak (FIG. 1), which indicates the material is an amorphous solid. The glass transition temperatures (Tg) was 14° C. The DSC data was obtained on a Q1000 Differential Scanning calorimeter (TA Instruments) at a rate of 10° C./min from −50 to 200 to −50° C.

Figure 2:
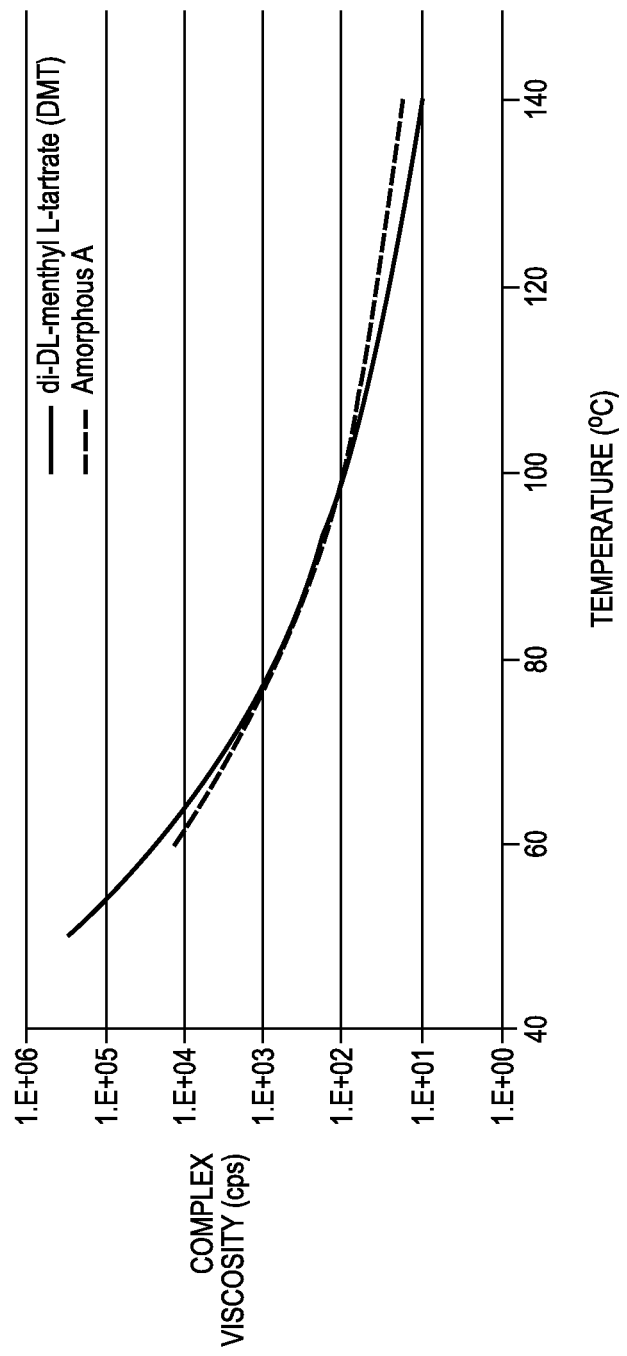
FIG. 2 is a graph illustrating rheology data of an exemplary amorphous component according to embodiments of the present disclosure.

As shown in FIG. 2, a rheology curve of Amorphous A is very similar to that of DMT (di-DL-menthyl L-tartrate). Amorphous A has relatively low viscosity (<$10^2$ cps) at high temperatures (>100° C.), but very high viscosity (>$10^5$ cps) at room temperature. Amorphous B also exhibited Tg=10° C., viscosity at 140° C.=17 cps, viscosity at room temperature >$10^5$ cps.

Preparation of Phase Change Ink

An ink sample was formulated from Amorphous A, a crystalline diurethane component (e.g., dibenzyl hexane-1,6-diyldicarbamate herein as DHDC), and a dye. The formulation is shown in Table 1 and the ink sample was labeled as Ink A.

TABLE 1

Ink formulation of Ink A.

| Component | Ink A Relative Parts (% wt) | Weight (g) |
|---|---|---|
| DHDC | 78.4 | 3.92 |
| Amorphous A | 19.6 | 0.98 |
| Solvent Blue 101 (Keyplast) | 2 | 0.1 |
| Total | 100 | 5 |

Synthesis of DHDC—Into a 16 oz jar equipped with magnetic stir was charged 120 g benzyl alcohol (MW=108, 1.11 mmol) and 10 drops of Fascat 4202 catalyst. The jar was placed in an about 130° C. oil bath. Then 93.3 g 1,6-hexamethylene diisocyanate (MW=168, 0.56 mmol) was added. Exothermal was observed. IR showed no isocyanate peak after 1 hour of reaction time. The reaction contents were poured into a tin pan to cool and solidify.

Figure 3:
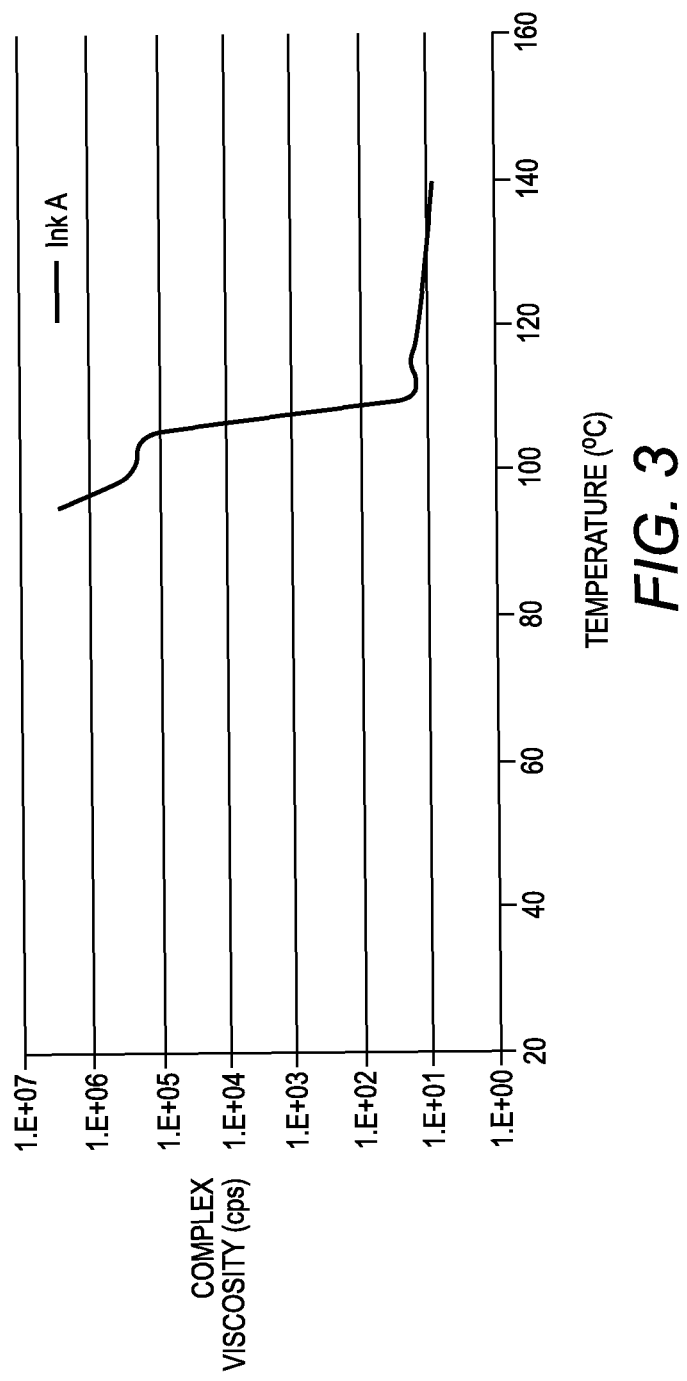
FIG. 3 is a graph illustrating rheology data of an exemplary ink composition according to embodiments of the present disclosure.

FIG. 3 shows rheology data of Ink A. The ink showed sharp phase transition to >$10^6$ cps at around 110° C., and the phase transition temperature can be adjustable by changing the crystalline/amorphous ratio within the desirable temperature range (60° C.<T<140° C.). The viscosity at 140° C. was about 9 cps, which was low enough to jet. The viscosity at 130-135° C. was about 10-11 cps, which was an accurate predictor of jetting temperature.

All of the rheology measurements were made on a RFS3 Rheometer (TA instruments), using a 25 mm parallel plate, at a frequency of 1 Hz; the method used was a temperature sweep from high to low temperatures, in temperature decrements of 5° C., a soak (equilibration) time of 120 seconds between each temperature and at a constant frequency of 1 Hz).

Print Performance

Ink A was printed onto Xerox® Digital Color Elite Gloss, 120 gsm (DCEG) coated papers using the K-proofer gravure printing plate, which is rigged with a pressure roll set at low pressure. The gravure plate temperature was set at 142° C., but the actual plate temperature is about 134° C. The K-proofer apparatus (manufactured by RK Print Coat Instrument Ltd., Litlington, Royston, Heris, SG8 0OZ, U.K.) is a useful printing tool to screen a variety of inks at small scale and to assess image quality on various substrates. The inks gave robust images that could not be easily removed from the substrates. When a metal tip with a curved tip at an angle of about 15° from vertical, with a weight of 528 g applied, was drawn across the image at a rate of approximately 13 mm/s no ink was visibly removed from the image. The tip is similar to a lathe round nose cutting bit with radius of curvature of approximately 12 mm.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. Unless specifically recited in a claim, steps or components of claims should not be implied or imported from the specification or any other claims as to any particular order, number, position, size, shape, angle, color, or material.

All the patents and applications referred to herein are hereby specifically, and totally incorporated herein by reference in their entirety in the instant specification.

What is claimed is:

1. A composition that is amorphous, the composition comprising:
at least one non-ester material and at least one ester of malic acid having a formula of

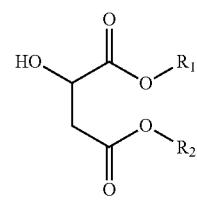

wherein $R_1$ and $R_2$ each, independently of the other, is an alkyl group, and further wherein the alkyl portion can be straight, branched or cyclic, saturated or unsaturated, substituted or unsubstituted, having from 1 to about 40 carbon atoms, an substituted or unsubstituted aromatic or heteroaromatic group, and mixtures thereof, wherein the at least one non-ester material and the at least one ester of malic acid are reaction products from the malic acid and one or more alcohols;
wherein the one or more alcohols comprise benzhydrol.

2. The composition of claim 1, wherein the malic acid is selected from the group consisting of DL-malic acid, a D-malic acid, an L-malic acid, and mixtures thereof.

3. The composition of claim 1, wherein the one or more alcohols further comprise an alcohol selected from

[structures: cyclohexanol; benzyl alcohol; 1-phenoxy-2-propanol; 2-phenoxyethanol; dicyclopentadienyl methanol; cyclohexanol (stereo); 2-hydroxyethyl salicylate; benzhydrol; 4-tert-butylcyclohexanol; 2-phenylethanol]

and mixtures thereof.

4. The composition of claim 1, wherein the amount of the one or more alcohols is from about 1 to about 5 equivalent moles based on 1 equivalent of the malic acid.

5. The composition of claim 1, wherein the amount of the benzhydrol is from about 1 to about 3 equivalent moles based on 1 equivalent of the malic acid.

6. The composition of claim 1, wherein the composition comprises:

[structure: dibenzhydryl 2-hydroxysuccinate]

7. The composition of claim 6, wherein the composition further comprises:

[structure]

8. The composition of claim 6, wherein the composition further comprises the following:

[structures], and

9. A composition that is amorphous, the composition comprising:

at least one non-ester material and at least one ester of malic acid having a formula of

[structure with $R_1$ and $R_2$]

wherein R₁ and R₂ each, independently of the other, is an alkyl group, and further wherein the alkyl portion can be straight, branched or cyclic, saturated or unsaturated, substituted or unsubstituted, having from 1 to about 40 carbon atoms, an substituted or unsubstituted aromatic or heteroaromatic group, and mixtures thereof;

wherein the at least one non-ester material and the at least one ester of malic acid are reaction products from the malic acid and one or more alcohols, wherein the one or more alcohols comprise benzhydrol; and wherein the composition has a viscosity of from about 1 to about 100 cps at a temperature from about 100° C. to about 140° C.

10. The composition of claim 9, wherein the one or more alcohols further comprise an alcohol selected from

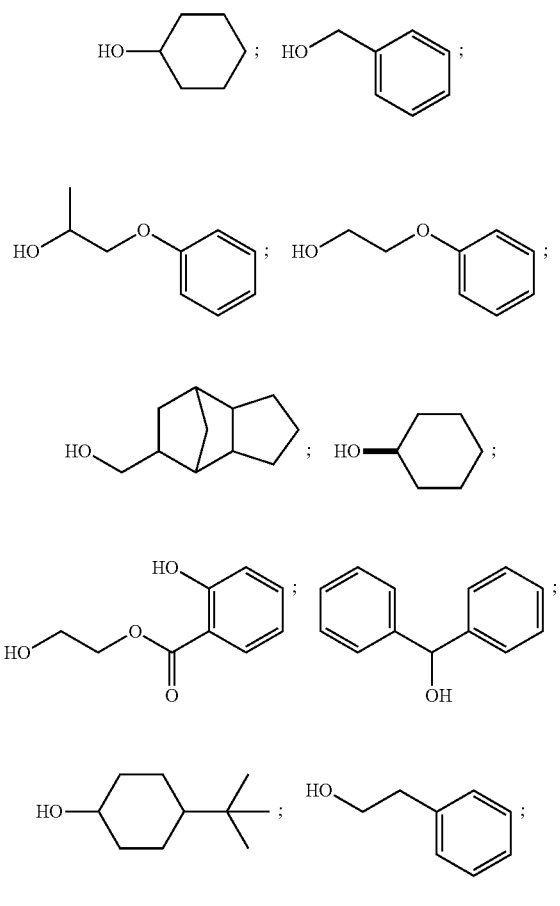

and mixtures thereof.

11. A method of forming a composition, the method comprising:

selecting at least one alcohol;

reacting the at least one alcohol with a malic acid; and controlling one or more reaction conditions to form the composition that is amorphous, wherein the composition comprises at least one non-ester material and at least one ester of malic acid having a formula of

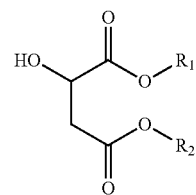

wherein R₁ and R₂ each, independently of the other, is an alkyl group, and further wherein the alkyl portion can be straight, branched or cyclic, saturated or unsaturated, substituted or unsubstituted, having from 1 to about 40 carbon atoms, an substituted or unsubstituted aromatic or heteroaromatic group, and mixtures thereof, wherein the at least one non-ester material and the at least one ester of malic acid are reaction products from the malic acid and one or more alcohols;

wherein the one or more alcohols comprise benzhydrol.

12. The method of claim 11, wherein the controlling of the one or more reaction conditions comprises controlling an acidic condition.

13. The method of claim 11, wherein the malic acid backbone is selected from the group consisting of DL-malic acid, a D-malic acid, an L-malic acid, and mixtures thereof.

14. The method of claim 11, wherein the selecting of at least one alcohol comprises selecting benzhydrol.

15. The method of claim 11, wherein the at least one alcohol further comprises an alcohol selected from

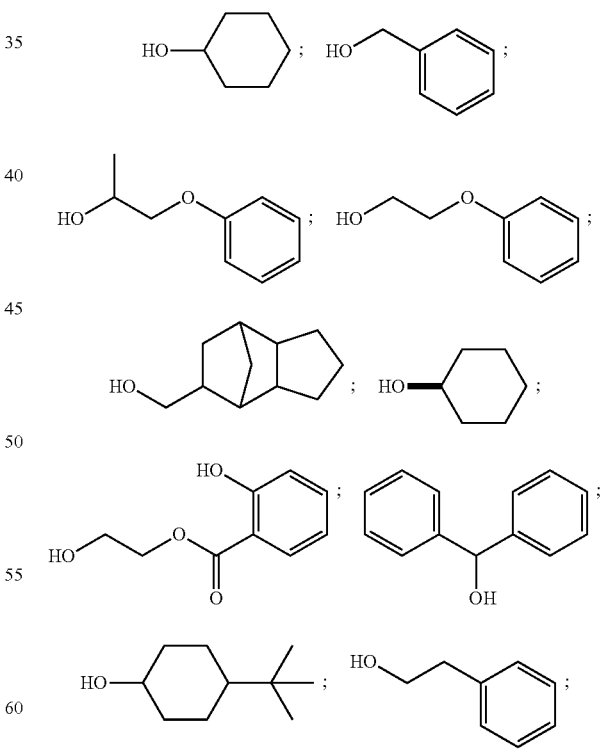

and mixtures thereof.

16. The method of claim 11, wherein the reacting of the at least one alcohol with the malic acid comprises the following reaction:

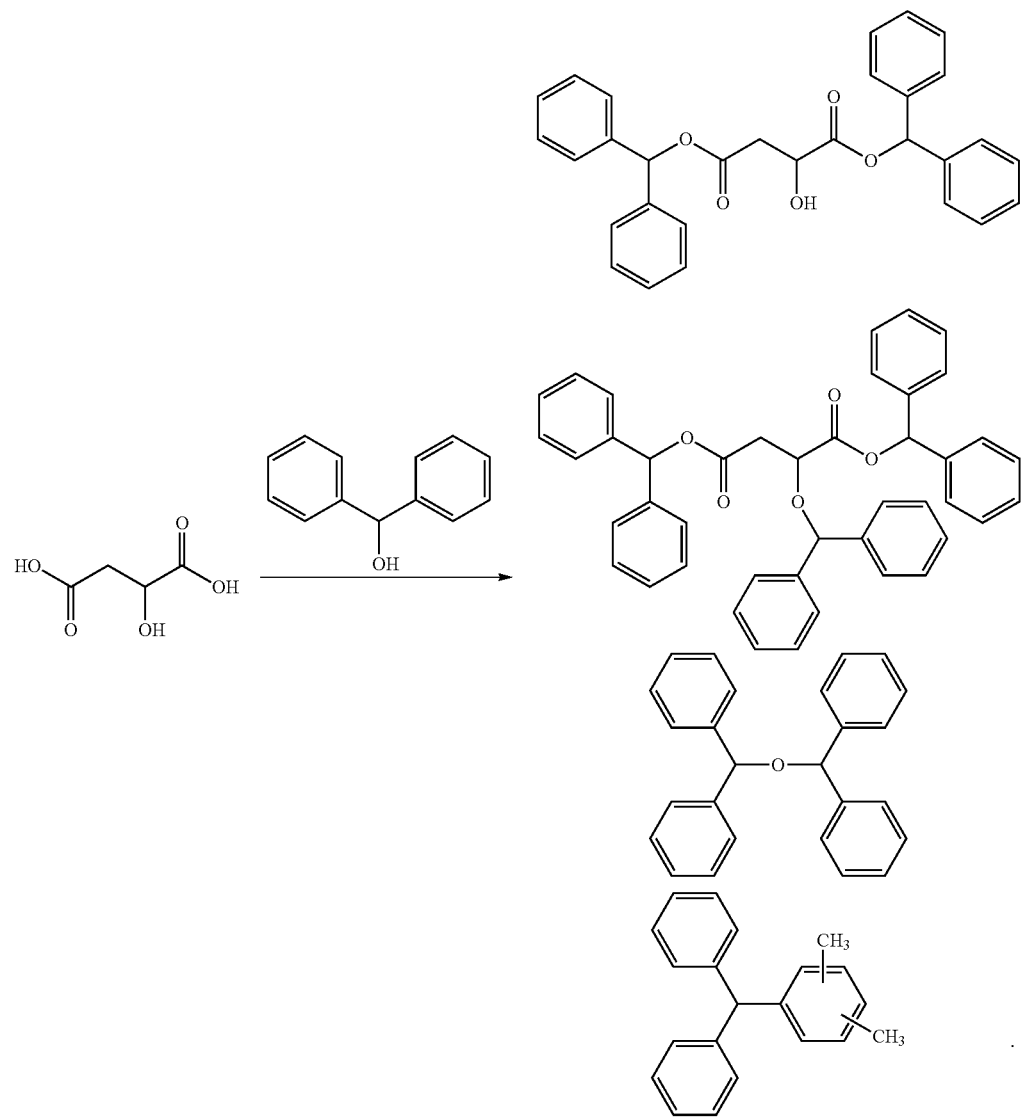
* * * * *